United States Patent [19]

Vanhumbeeck et al.

[11] 4,165,218

[45] Aug. 21, 1979

[54] MONITORING SURFACTANT IN ELECTROLYTE DURING METAL TREATMENT

[75] Inventors: Jacky Vanhumbeeck, Brugge; Christiaan Vandenbossche, Zwijnaarde, both of Belgium

[73] Assignee: Siemens Aktiengesellschaft, Berlin & Munich, Fed. Rep. of Germany

[21] Appl. No.: 845,045

[22] Filed: Oct. 25, 1977

[30] Foreign Application Priority Data

Nov. 4, 1976 [DE] Fed. Rep. of Germany ....... 2650572

[51] Int. Cl.$^2$ .................... G01N 31/16; G01N 21/02; C25D 3/30
[52] U.S. Cl. .............................. 23/230 R; 23/230 A; 23/230 M; 422/75; 422/110; 204/54 R
[58] Field of Search ............ 23/230 R, 230 A, 230 M, 23/253 R, 253 A; 204/54 R; 356/208; 422/75, 108, 110, 62, 68, 105

[56] References Cited

U.S. PATENT DOCUMENTS

| | | | |
|---|---|---|---|
| 2,464,846 | 3/1949 | Buser | 23/230 R |
| 2,977,199 | 3/1961 | Quittner | 23/230 R |
| 3,361,652 | 1/1966 | Korplun et al. | 204/54 R |
| 3,422,271 | 1/1969 | Fuhrmann | 23/254 R X |
| 3,462,244 | 8/1969 | Leisey | 23/230 R |
| 3,731,807 | 5/1973 | Louboutin et al. | 23/253 R X |
| 3,838,926 | 10/1974 | Kato et al. | 356/208 |
| 3,870,466 | 3/1975 | Rellstab et al. | 23/253 R X |

Primary Examiner—Scovronek
Attorney, Agent, or Firm—Hill, Van Santen, Steadman, Chiara & Simpson

[57] ABSTRACT

A technique for the quantitative monitoring of a nonionic surfactant, such as nonylphenolpolyglycolether, in an acid tinning bath for the production of shiny, pore-free coatings on components. A measured amount of bath fluid (a bath specimen) is diluted with distilled water and mixed with sulfuric acid, and this mixture is then immediately titrated with a tannic acid solution until opalescence occurs.

4 Claims, 3 Drawing Figures

1

MONITORING SURFACTANT IN ELECTROLYTE DURING METAL TREATMENT

BACKGROUND OF THE INVENTION

By one procedure in the prior art, the amount of wetting agent contained in an acidic tin-lead bath is determined, for example, by taking 10.0 ml of the bath fluid, mixing it with about 80.0 ml of distilled water, and adding 20.0 ml of dilute nitric acid. The diluted and acidified bath specimen is slowly titrated by means of a tannic acid solution until opalescence remains. The tannic acid solution used for titration contains about 1 gm of tannic acid per liter of distilled water. The nitric acid serving as mixing agent for the diluted bath fluid is thinned to a ratio of about 1:5. When titrating the bath specimen and when determining the quantitative level of surfactant or wetting agent in the bath specimen, the amount of tannic acid solution consumed up to the point where opalescence remains (persists) is measured. However, the effective component of the tannic acid solution is not constant which makes it necessary to carry out a second titration with the same bath fluid and which is accomplished adding a measured amount of a standard surfactant solution. The quantitative level of surfactant in the bath specimen is established by calculation from the two values measured for the amount of tannic acid solution used. To determine the titration point, use is made of a base which is as black as possible and which serves as a contrasting background to confirm when opalescence remains.

This known procedure described above has proven its worth for acid tin-lead baths; however, it is not suitable for automatically establishing the level of nonionic surfactant in acid tinning baths because of the fact that the bath fluid in tinning baths exhibits a comparatively high degree of natural cloudiness and becomes even cloudier when dilute nitric acid is added before titration even starts. Precise recognition of the final point is consequently precluded. In addition, a visual recognition of the final titration point cannot be mechanised. It must be merely assumed that, during titration, the commencement of the clouding process is influenced by other substances contained in the bath fluid in the bath to be tested. Consequently, the final or titration point cannot be determined with the sufficient precision required in precise automated processing.

BRIEF SUMMARY OF THE INVENTION

The present invention relates to an apparatus and a process for quantitatively monitoring the quantity of nonionic surfactant in an acid tinning bath, particularly one of the type used for the production of shiny, pore-free coatings on manufactured components.

A primary object of the invention is to improve the above-described prior art technique in such a way that it can be used for automatic quantitative monitoring of the level of a nonionic surfactant in an acid bath fluid containing tin sulphate and sulphuric acid apart from other additives.

Other and further objects, purposes, advantages, aims, utilities, features and the like will be apparent to those skilled in the art from a reading of the present specification taken together with the drawings.

DETAILED DESCRIPTION

Figure 1:
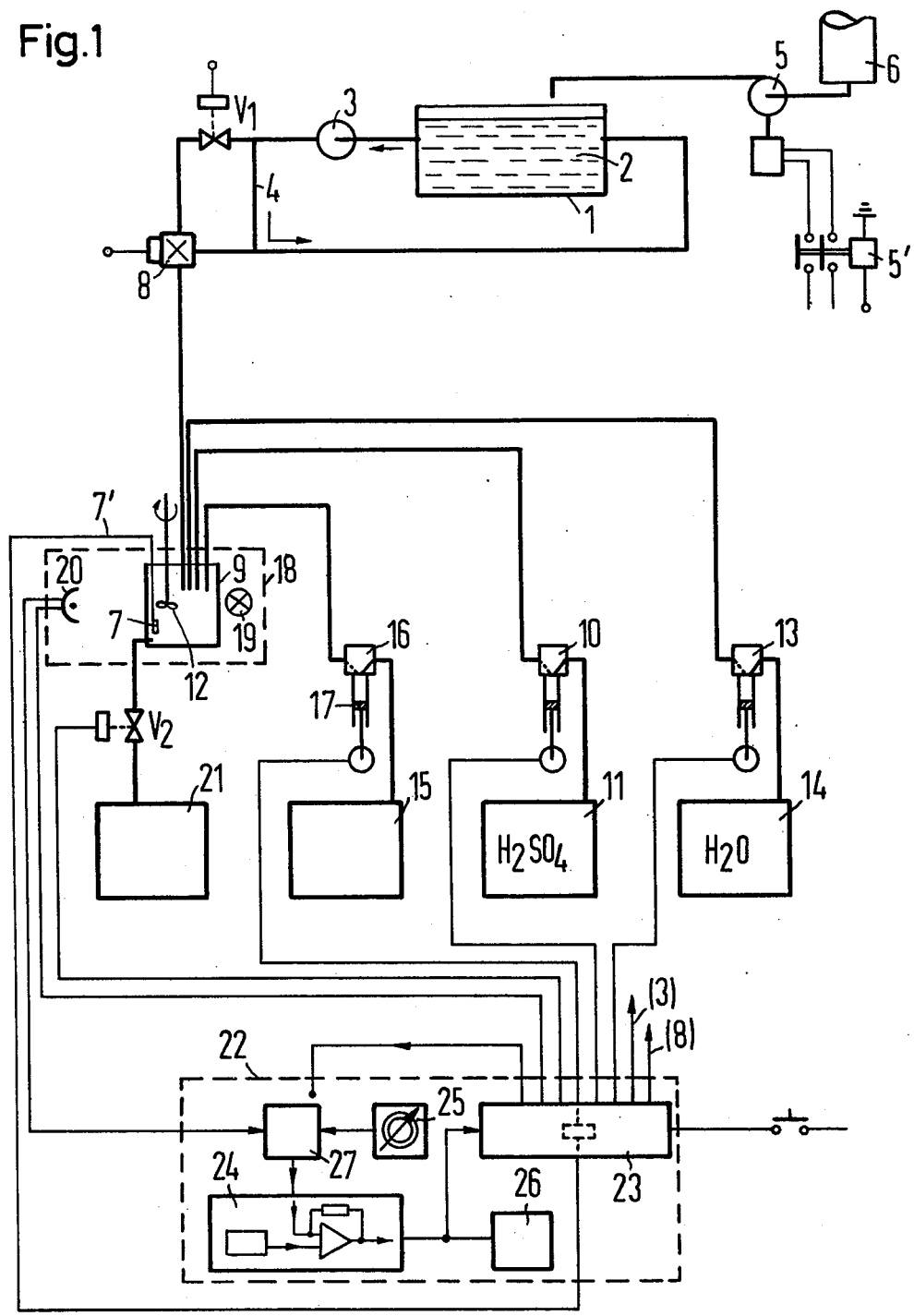
FIG. 1 shows one embodiment of a device for monitoring the level of surfactant in an acidic tinning bath in accord with the teachings of the present invention.

In accordance with the present invention, prior to titration, the bath fluid is first mixed with sulphuric acid, and distilled water is added to the bath specimen at once. In addition, the final titration point is fixed photometrically and evaluated automatically by computation. The titration solution is added to the bath specimen at a constant rate at constant intervals, and the corresponding difference in output voltage at the photometer is measured in the interval. When a constant voltage difference is measured in two successive measurements, the proportionality factor between voltage difference and titration volume is determined. The lowest value for the titration volume representing the final titration point is established from these values by retrogressive interpolation of the line passing through the points of constant voltage difference.

When one proceeds in this way, the known method as modified by the present invention can be mechanized, as described and illustrated herein. When use is made of sulphuric acid for mixing the bath specimen as well instead of nitric acid with such acid tinning baths, and then distilled water is added to the fluid to be tested for further dilution of the bath specimen, the bath fluid does not become cloudy. However, as before, there is still the disadvantage that when titrating with tannic acid solution, the final titration point cannot be fixed satisfactorily. As already indicated, the bath fluid also contains a number of other components which during titration cause gradual clouding as the titration solution is added to the bath specimen. However, the final titration point can be established with sufficient precision by calculation. As soon as the voltage signal at the output of a photometer rises in proportion with the addition of the titration solution, on the flat part of a characteristic S-curve, these measurement points lie on a straight line which is made to intersect the abscissa of a co-ordinate system, thereby indicating the titration volume. The point of intersection between the straight line and the abscissa indicates the final titration point with a high degree of accuracy. This inventive procedure for establishing the final titration point makes it possible for the calibration line determined with standard solutions to be linear, and to pass through the origin; these conditions are much desired for working in standardized conditions.

As far as practical, and possible a titration should be carried out at a constant temperature preferably within a temperature range of ±1° C. maximum at room temperature, that is about 20° C. When use is made of a stirrer, as preferred in accordance with the invention, it is particularly advantageous to offset the effect of the titration solution influenced by the temperature by a controlled modification of the titration volume in relation to the measured temperature at which the titration is being carried out. Preferably, the photometric measurement is carried out turbidometrically. A measurement signal obtained in this way is more reliable in the region of the final titration point than one obtained by way of a nephelometric evaluation of the final point. Since the complete establishment of the clouding is a factor of time, the titration speed should preferably be constant and not more than about 1 ml/min. Once the final titration point is known, the level of wetting agent or surfactant in the bath specimen can be determined with reference to a calibration line, or to a constant conversion factor.

It has been found that the other bath components, such as the tin dissolved in the bath, and the sulphuric acid, have no effect on the practice of the invention characteristically up to at least double the usual nominal concentration. When adding a fresh tannic acid solution, it can happen that its action differs from that of the original tannic acid solution, or does not match the calibration line for the latter solution. When necessary or desirable, the original calibration line can then be adapted to match the new titration solution.

For example, referring to FIG. 1, a bath 1 contains tin sulphate, sulphuric acid, redox reagents, and other additives, and in particular, a surfactant, in an aqueous solution. The amount of surfactant contained in the bath 1 is constantly monitored with regard to its percentage volume and is made up in the event of a departure from the nominal or chosen standard level. The bath fluid 2 is constantly kept in motion through a circuit 4 by means of a circulating pump 3. As the concentration of wetting agent drops through continuous use of the bath, a metering pump 5 is set in operation so that wetting agent runs into the tinning bath from a surfactant solution concentrate storage unit 6. To establish the level of surfactant in the bath fluid, a measured amount of fluid is removed from the bath circuit at set intervals of time by controlled opening a valve V1 and is passed to quantity-limiting unit 8; this amounts for example, to about 2.5 ml for a bath of the kind named. From such quantity-limiting unit 8, the now precisely measured bath specimen is fed to a reaction vessel 9. By means of a metering cylinder 10, which is connected to a storage vessel 11 containing sulphuric acid solution, 10 ml, for example, of sulphuric acid solution are released into the reaction vessel 9. Metering cylinder 10 is calibrated to discharge, for example, 5 ml per stroke, so that a desired amount of sulphuric acid passes into the bath specimen with, for example, two discharge strokes. The bath specimen already containing sulphuric acid is stirred in with the added sulphuric acid using a stirrer 12. Then, for example, 40 ml of distilled water are added to the bath specimen by means of a metering cylinder 13 connected to a storage vessel 14 containing distilled water. This metering cylinder 13 is calibrated to, for example, 20 ml charges, so that this pump also utilizes two discharge strokes to so charge.

The prepared bath specimen is immediately titrated with tannic acid solution (for example, 1 g/l). Such titration is carried out using a motorized piston-type burette 16 which is connected to a storage vessel 15 holding tannic acid solution. The titration is carried out, for example, by the titration piston 17 advancing over a measured distance such that a suitable volume of titration solution continuously flows into the reaction vessel. It has been found that the formation of the clouding in the bath specimen is also dependent upon time. Consequently, the titration speed should preferably be less than about 1 ml/min. The reaction vessel 9 holds a heat sensor 7 the output 7' of which is connected up to a computer 22.

The reaction vessel 9 also serves as a filter trough for a photometer 18, indicated symbolically by an emitter 19 and the receiver 20, for measuring the intensity of a beam of light (not detailed) passing through the filter trough 9. On completion of the titration, the bath fluid contained in the reaction vessel 9 is released into a waste container 21 by automatically opening the valve V2. The bath fluid is analyzed again for surfactant concentration after each predetermined time interval of operation, such as a time interval ranging from about 0.5 to 1 hour of operation.

The measuring signal of the receiver 20 is also passed to the computer 22. The computing operation performed by computer 22 is explained below.

The computer 22 contains a process control section 23 to control electromechanical or pneumatic devices, such as the valves, the metering cylinders, the burettes, and the like. The computer 22 incorporates a controller (such as one commercially available under the trade designation "Intel 8008" or "Intel 8080", such as is described in the booklet "From CPU to Software" published by Intel Corporation 1974, printed USA, 3065 Bowers Avenue, Santa Clara, California). With such apparatus the programming can be by tape, punched tape, or similar means. The computer 22 contains a temperature compensator 27 together with a conventional type "nominal"/"real" comparator 24 which sends a control signal to the metering pump 5, according to the signal difference measured between nominal and real values. The temperature compensator corrects the measuring signal of the receiver of the photometer. According to the magnitude of the difference measured, the running time of the constant operating speed metering pump 5 is varied, and thus the amount of surfactant flowing into the tinning bath is measured and regulated. The light-sensitive element 20 of the photometer 18 is aligned on the beam of light for turbidometric measurement.

Figure 2:
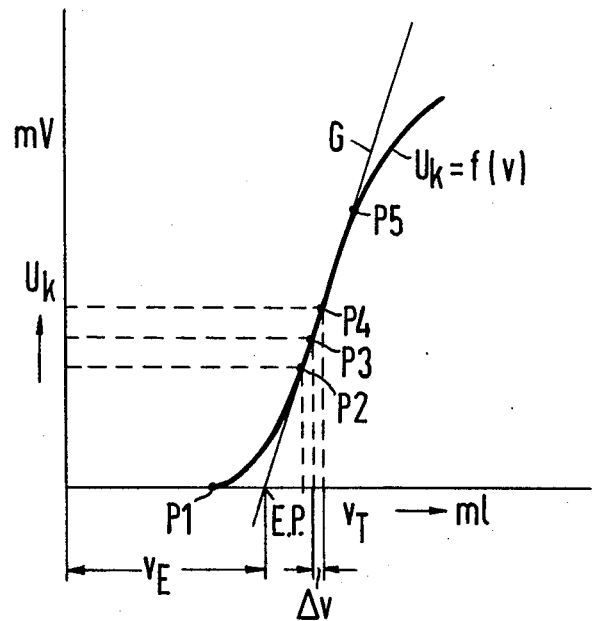
FIG. 2 is a plot showing and illustrating exemplarily the relationships between the temperature compensated voltage signal $V_R$ of the light sensitive element (as ordinates) and the tannic acid solution $V_T$ added to a specimen solution (as abscissae)

For a co-ordinate system for a bath fluid of the kind above indicated, FIG. 2 shows the voltage pattern of the photometer signal during titration of the bath specimen. The tannic acid solution $v_T$ added to a specimen or test fluid is plotted in ml on the abscissa and the voltage signal $U_k$ of the light sensitive element 20 modified by the temperature compensator is plotted on the ordinate. After a predeterminable amount of tannic acid solution has been added, the test fluid gradually becomes cloudy at a point P1. This results in a signal voltage rise. From point P2 onwards, the rise in voltage $U_k$ is proportional to the amount of tannic acid solution added. The gradual rise in the voltage signal in the curve path P1, P2 is due to the test fluid containing a number of other substances in addition to the surfactant so that the point where clouding sets in is not sudden. The real starting point E.P. must therefore be calculated by retrogressive interpolation.

Due to the fact that the rise in voltage $U_k$ is proportional to the amount of titration solution added from point P2 onwards, a straight line G can be plotted. The point of intersection of line G with the abscissa indicates with a high degree of precision the amount of titration solution, namely the tannic acid solution, $v_E$, added up to the point where the cloudiness sets in. This operation to establish the starting point E.P. is also carried out by the computer 22 (see FIG. 1). Advantageously, titration is continued until a point such as point P5, for example, is reached where there is no further rapid increase in the voltage of the measuring signal proportional to the amount of tannic acid solution added. The computer 22 determines this point at which the measuring signal rises slowly in comparison with the amount of tannic acid solution added and, at this point, computer 22 then emits a switching signal to the process control section 23.

Figure 3:
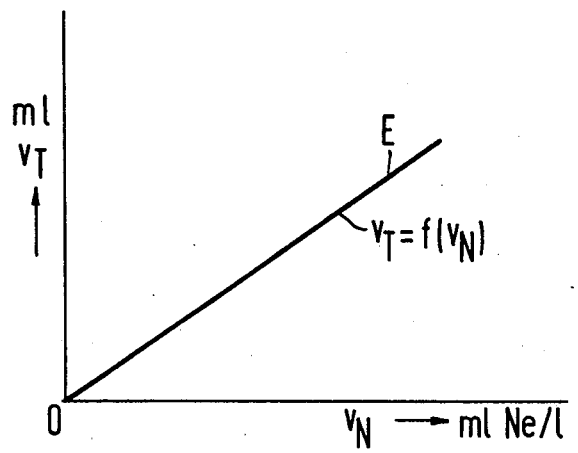
FIG. 3 is a plot showing and illustrating exemplarily, a calibration line between volume of titration fluid (as ordinates) and amount of surfactant (as abscissae).

Then calibration line E shown in FIG. 3 shows how the volume of titration solution added up to point E.P. is dependent upon the amount of surfactant contained in a unit volume of bath fluid when using a specific quantity of tannic acid in solution. Because the graph line passes through the origin, the quantitative level of surfactant Vn per ml of bath fluid can be determined on the calibration line for a specific amount of tannic acid solution, for instance $v_E$ (see FIG. 2). Consequently, a conversion factor corresponding to the calibration line G is obtained for a specific tannic acid solution to establish the concentration of surfactant in the bath fluid. This factor can be fed into the computer 22 by means of the input 25 (see FIG. 1). The nominal-value comparator 24 supplies the difference signal which is applied to a timer 26. This timer 26 converts the voltage difference signal from the nominal-value comparator 24 into a proportional continuous signal. As long as this continuous signal is present, the switch 5' to the metering pump remains closed so that, as described above, there is delivered a suitable amount of surfactant into the tinning bath 1.

Although the teachings of our invention have herein been discussed with reference to specific theories and embodiments, it is to be understood that these are by way of illustration only and that others may wish to utilize our invention in different designs or applications.

We claim:

1. In a method for the quantitative monitoring of a nonionic surfactant, in an acid tinning bath of the type employed for the production of shiny, pore-free coatings on component parts, in which method a measured sample of bath fluid is diluted with distilled water, mixed with an acid, and the resulting mixture is titrated with a tannic acid solution until opalescence persists, the improvement which comprises the steps of:
   (A) mixing with such a sample of bath fluid sulfuric acid as such acid,
   (B) then mixing therewith distilled water,
   (C) then automatically adding tannic acid to the resulting sample of bath fluid while concurrently monitoring such resulting sample photometrically, said tannic acid being so added as an aqueous solution to such resulting sample at a constant rate and at constant intervals of time, and the corresponding difference in the output voltage photometrically being measured in each interval of no tannic acid addition, and then, when a constant voltage difference is found between two successive such measurements,
   (D) calculating the proportionality factor between such voltage difference and the titration volume and determining the lowest value for the titration volume as representing the final titration point from such calculated values by retrogressive interpolation of the straight line passing through the points of constant voltage difference.

2. The method of claim 1 wherein such photometric measurement is carried out turbidimetrically.

3. Apparatus for quantitatively monitoring a nonionic surfactant in an acid tinning bath comprising
   means for automatically extracting a sample from such bath
   means for automatically admixing with such sample a fixed amount of a first acid liquid,
   means for thereafter automatically admixing with such sample a fixed amount of water,
   means for automatically charging at a constant rate and at constant predetermined regular intervals of time a titration acid liquid to the resulting liquid mixture,
   photometer means adapted to measure the turbidity of said resulting liquid mixture and for generating a voltage signal representative of turbidity so sensed,
   operating means for causing said photometer means to so measure when said means for charging is between said charging intevals,
   means for measuring the titration volume and for generating a signal representative thereof,
   means for calculating a proportionality factor between said signal representative of said titration volume and said signal representation of said photometric measurement,
   means for determining the lowest value for such titration volume as representing the final titration point from such calculated proportionality factors by retrogressive interpolation of the straight line passing through points of a constant voltage difference sensed by successively made constant values of said signal representative of said photometric measurement.

4. The apparatus of claim 3 additionally incorporating means for sensing the instantaneous temperature of said sample and for generating a signal representative thereof, and means for modifying the titration volume in relation thereto.

* * * * *